US00PP35209P2

(12) United States Plant Patent
Smith

(10) Patent No.: US PP35,209 P2
(45) Date of Patent: Jun. 6, 2023

(54) ***CHRYSANTHEMUM* PLANT NAMED 'CIFZ0090'**

(50) Latin Name: ***Chrysanthemum* x *morifolium***
Varietal Denomination: CIFZ0090

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/581,131

(22) Filed: Jan. 21, 2022

(51) Int. Cl.
*A01H 5/02* (2018.01)
*A01H 6/14* (2018.01)

(52) U.S. Cl.
USPC ..... Plt./290
CPC ..... *A01H 6/1424* (2018.05)

(58) Field of Classification Search
USPC ..... Plt./290
CPC ..... A01H 6/1424
See application file for complete search history.

*Primary Examiner* — Anne Marie Grunberg
(74) *Attorney, Agent, or Firm* — Dale Skalla

(57) ABSTRACT

A new garden type *Chrysanthemum* plant named 'CIFZ0090' particularly distinguished by its small to medium sized plant with round plant habit, a medium size decorative flower with rich fall tone bronze flower color when viewed naturally, and a natural season response early to mid-October.

1 Drawing Sheet

Figure 1:
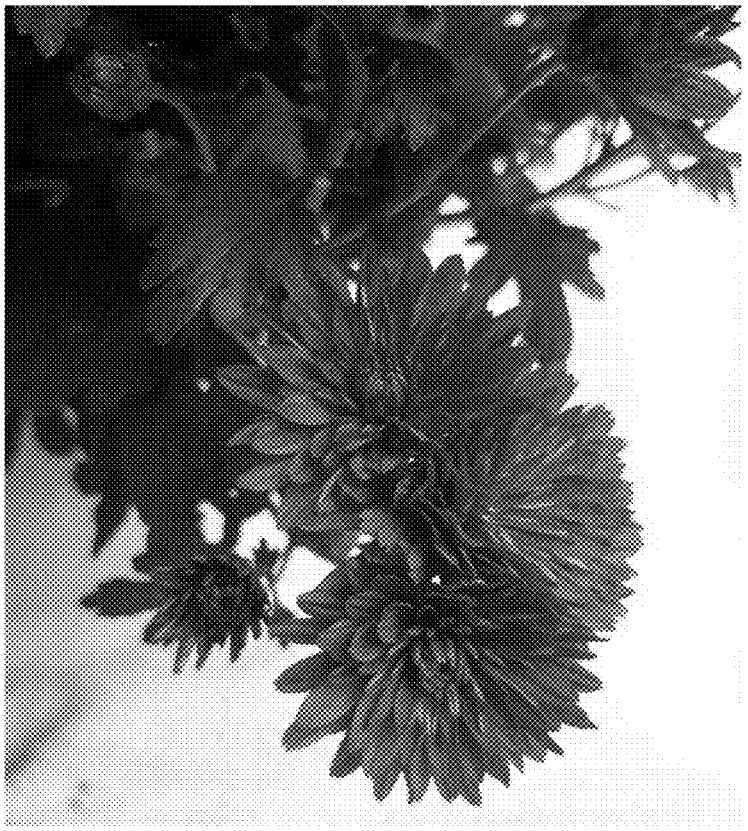

Latin name of the genus and species of the plant claimed: *Chrysanthemum* x *morifolium*.

Varietal denomination: 'CIFZ0090'.

BACKGROUND OF THE NEW PLANT

The present invention comprises a new *Chrysanthemum*, botanically known as *Chrysanthemum* x *morifolium*, and hereinafter referred to by the variety name 'CIFZ0090'.

'CIFZ0090' is a product of a planned breeding program. The new cultivar has a small to medium sized plant with round plant habit, medium sized decorative flowers with rich fall tone bronze flower color when viewed naturally, and a natural season response early to mid-October.

'CIFZ0090' originated from a cross made in November 2014 in Enkhuizen, The Netherlands. Seeds were sown in November 2016 in Gilroy, Calif. and 'CIFZ0090' was selected from the resulting population on Mar. 28, 2017 in Alva, Fla.

The female parent was an unnamed proprietary seedling '13-M139'.

TABLE 1

Characteristics of the female parent, compared to 'CIFZ0090':

| Trait | 'CIFZ0090' | '13-M139' |
|---|---|---|
| Natural response: | Similar | Similar |
| Blackcloth response: | Slower | Faster |
| Flower size: | Similar | Similar |
| Flower color: | Bronze-orange | Red |
| Flower type: | Similar | Similar |
| Plant size: | Similar | Similar |
| Plant habit: | Similar | Similar |

The male parent was an unnamed proprietary seedling '13-M453'.

TABLE 2

Characteristics of the male parent, compared to 'CIFZ0090':

| Trait | 'CIFZ0090' | '13-M453' |
|---|---|---|
| Natural response: | 1 week slower | 1 week faster |
| Blackcloth response: | Similar | Similar |
| Flower size: | Similar | Similar |
| Flower color: | Bronze-orange | Bronze-coral |
| Flower type: | Less disk florets | More disk florets |
| Plant size: | Smaller | Larger |
| Plant habit: | Less wide | Wider |

The first act of asexual reproduction of 'CIFZ0090' was accomplished when vegetative cuttings were propagated from the initial selection in June 2017 in Alva, Fla.

BRIEF SUMMARY OF INVENTION

Horticultural examination of plants grown from cuttings of the plant initiated in January 2017 and continuing thereafter, has demonstrated that the combination of characteristics as herein disclosed for 'CIFZ0090' are firmly fixed and are retained through successive generations of asexual reproduction.

'CIFZ0090' has not been observed under all possible environmental conditions. The phenotype may vary significantly with variations in environment such as temperature, light intensity and day length.

A Plant Breeder's Right for this cultivar has not yet been applied for. 'CIFZ0090' has not been made publicly available prior to the effective filing date of this application, notwithstanding any disclosure that may have been made less than one year prior to the effective filing date of this application by the inventor or another who obtained 'CIFZ0090' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0090' with colors being as true as possible with an illustration of this type. The photographic drawing shows in FIG. 1 a close view of flower of the new variety and in FIG. 2 a flowering plant from an outdoor trial.

Figure 2:
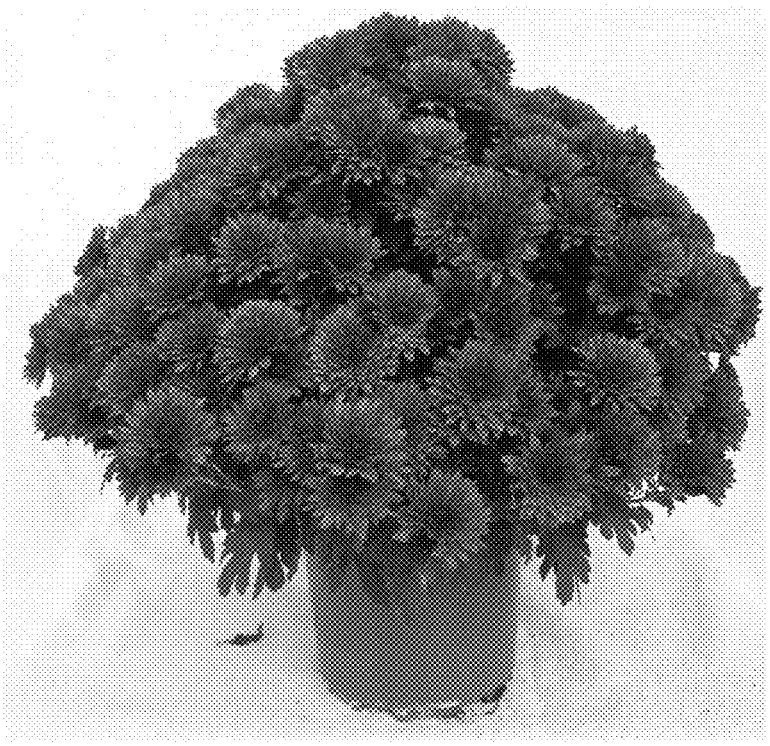

The aforementioned photographs: FIG. 1, as well as FIG. 2, were taken on Sep. 8, 2021 both showing a plant from the same blackcloth outdoor trial in Enkhuizen, The Netherlands.

These plants were about 13 weeks of age. One rooted cutting per pot had been planted in a 19 cm pot, not pinched in week 23, 2021 and black clothed from week 29. Plants started flowering the end of August 2021.

The measurements were taken in Enkhuizen, The Netherlands, in September, 2021 on plants from the same outdoor blackcloth trial.

DETAILED BOTANICAL DESCRIPTION

Color references are made to The Royal Horticultural Society Colour Chart (R.H.S.) 2001.

TABLE 3

DIFFERENCES BETWEEN THE NEW VARIETY 'CIFZ0090' AND TWO MOST SIMILAR VARIETIES:

| Trait | 'CIFZ0090' | 'Stephany Bronze', Not patented |
|---|---|---|
| Natural response: | ½ week faster | ½ week slower |
| Blackcloth response: | ½ week faster | ½ week slower |
| Flower size: | Similar | Similar |
| Flower color: | Darker, more bronze | Lighter, more yellow |
| Flower type: | Similar | Similar |
| Plant size: | Similar | Similar |
| Plant habit: | Similar | Similar |
| Flower longevity: | Color fades to orange | Color fades to yellow |

TABLE 4

| Trait | 'CIFZ0090' | 'Veritas Orange', U.S. Plant Pat. No. 25,254 |
|---|---|---|
| Natural response: | Similar | Similar |
| Blackcloth response: | ½ week slower | ½ week faster |
| Flower size: | Bit larger | Bit smaller |
| Flower color: | Darker, more reddish | Lighter, more orangish |
| Flower type: | Similar | Similar |
| Plant size: | Similar | Similar |
| Plant habit: | Similar | Similar |

Plant:

*Form, growth and habit.*—Herbaceous garden-type, stems Upright and outwardly spreading, freely branching, strong and moderately vigorous growth habit.

*Plant height (above soil).*—23 cm.

*Plant height (inflorescence included).*—26 cm.

*Plant width.*—45 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 147A.

*Immature leaf, color lower surface.*—RHS 147B.

*Mature leaf, color, upper surface.*—RHS 147A.

*Mature leaf, color lower surface.*—RHS 138B.

*Length.*—8.5 cm.

*Width.*—3.5 cm.

*Shape.*—Ovate, with distinct lobes.

*Base shape.*—Shortly attenuate.

*Apex shape.*—Acute.

*Margin.*—2-3 lobed.

*Number of margin indentations.*—Approximately 13.

*Depth of margin indentations.*—0.4 cm.

*Leaf length terminal lobe relative to total leaf length.*—1:3.

*Leaf depth lower lateral sinus.*—0.8-1.4 cm.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole length.*—1.5 cm.

*Diameter.*—0.3 cm.

*Texture.*—Bifid hairs.

*Presence of stipules.*—Not present.

Stem:

*Quantity of main branches per plant.*—9.

*Color of stem.*—RHS 146C.

*Length of stem.*—9.0-10.0 cm.

*Diameter.*—0.6 cm.

*Length of internodes.*—2.0-4.0 cm.

*Texture.*—Bifid hairs.

*Color of peduncle.*—RHS 146B.

*Length of peduncle.*—2.0-4.0 cm.

*Peduncle diameter.*—0.2 cm.

*Texture.*—Bifid hairs.

Inflorescence:

*Type.*—Compositae, solitary, decorative type inflorescences borne terminally above foliage, ligulate ray florets arranged in whorls on a capitulum giving a decorative flower.

*Quantity of short days to flowering (response time).*—Approximately 8 weeks.

*Quantity of inflorescences per plant.*—260 with several small buds developing.

*Lastingness of individual blooms on the plant.*—About four weeks from first color.

*Fragrance.*—Slightly spicy.

Bud (when showing color):

*Color.*—RHS N34A.

*Length.*—0.7 cm.

*Width.*—1.0 cm.

*Shape.*—Oblate.

Immature inflorescence (at moment of opening):
*Diameter.*—2.8 cm.
*Color of ray florets, upper surface.*—RHS 46B.
*Color of ray florets, lower surface.*—RHS 34C.
Mature inflorescence:
*Diameter.*—4.8 cm.
*Depth.*—2.0 cm.
*Total diameter of disc.*—0.0-0.4 cm.
*Receptacle color.*—RHS 138B.
*Receptacle height.*—0.5 cm.
*Receptacle diameter.*—1.0 cm.
*Length of corolla tube.*—0.4 cm.
Ray florets:
*Average quantity of florets.*—165 in several whorls.
*Color of florets, upper surface.*—RHS 42B.
*Color lower surface.*—RHS N34C.
*Length.*—2.0 cm.
*Width/diameter.*—0.4 cm.
*Shape.*—Oval.
*Apex shape.*—Emarginate.
*Base shape.*—Tube.
*Margin.*—Entire: Small incisions may be present at tip.
*Margin.*—Type of rolling: Involute.
*Texture, upper surface.*—Papillate.
*Lower surface.*—Papillate.
*Ribs present.*—Yes.
*Number of keels.*—1.
*Profile at widest point.*—Weakly concave.
*Longitudinal axis shape.*—Incurving.
*Longitudinal axis curvature strength.*—Medium.
*Corolla tube shape.*—Circular.
Disc florets:
*Number of disc florets.*—0-15.
*Width.*—0.1 cm.
*Length.*—1.2 cm.
*Color.*—RHS 13A.
Inflorescence (at moment of senescence):
*Color of ray florets, upper surface.*—RHS 42B.
*Color of ray florets, lower surface.*—RHS N34C.
Phyllaries:
*Quantity.*—20-25.
*Color, upper surface.*—RHS 138B.
*Color, lower surface.*—RHS 138D.
*Length.*—0.6 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.
Reproductive organs:
*Pistil.*—One.
*Length.*—0.4 cm.
*Style color.*—RHS 8D.
*Style length.*—0.3 cm.
*Stigma color.*—RHS 7D.
*Stigma shape.*—Bi-parted.
*Ovary color.*—RHS 130D.
*Ovary length.*—0.2 cm.
*Ovary width.*—0.1 cm.
Androecium:
*Stamens.*—1, found on only disc florets.
*Color of filaments.*—RHS 155C.
*Length filaments.*—0.2 cm.
*Anther color.*—RHS 13A.
*Anther length.*—0.2 cm.
*Anther shape.*—Oval to club shaped.
*Color of pollen.*—RHS 13A.
*Pollen amount.*—Sparse.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0090' substantially as illustrated and described herein.

* * * * *